(12) United States Patent
Hasenzahl et al.

(10) Patent No.: US 6,841,144 B2
(45) Date of Patent: Jan. 11, 2005

(54) METHOD FOR THE PRODUCTION OF A TITANIUM-CONTAINING ZEOLITE

(75) Inventors: Steffon Hasenzahl, Maintal (DE); Klaus Heyne, Bruchkobel (DE); Dieter Kneitel, Rodenbach (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 10/220,577

(22) PCT Filed: Feb. 24, 2001

(86) PCT No.: PCT/EP01/02118

§ 371 (c)(1),
(2), (4) Date: Sep. 3, 2002

(87) PCT Pub. No.: WO01/64581

PCT Pub. Date: Sep. 7, 2001

(65) Prior Publication Data

US 2003/0103894 A1 Jun. 5, 2003

(30) Foreign Application Priority Data

Mar. 2, 2000 (EP) .......................................... 00104324

(51) Int. Cl.$^7$ .......................... B01J 29/89; C01B 37/00; C06D 301/12
(52) U.S. Cl. ....................... 423/713; 423/326; 423/716; 502/214; 549/531
(58) Field of Search ................................ 423/713, 326, 423/716; 502/242; 549/531

(56) References Cited

U.S. PATENT DOCUMENTS

| | | | | |
|---|---|---|---|---|
| 4,410,501 A | * | 10/1983 | Taramasso et al. | 423/705 |
| 5,082,641 A | * | 1/1992 | Popa et al. | 423/326 |
| 5,466,835 A | * | 11/1995 | Nemeth et al. | 549/531 |
| 5,525,563 A | | 6/1996 | Thiele et al. | |
| 5,527,520 A | * | 6/1996 | Saxton et al. | 423/706 |
| 5,637,715 A | | 6/1997 | Thiele et al. | |
| 5,683,952 A | * | 11/1997 | Onozawa et al. | 502/242 |
| 5,688,484 A | * | 11/1997 | Saxton et al. | 423/700 |
| 5,758,778 A | | 6/1998 | Kershner | |
| 5,885,546 A | | 3/1999 | Kumar | |
| 5,919,430 A | | 7/1999 | Hasenzahl et al. | |
| 6,054,112 A | * | 4/2000 | Hasenzahl et al. | 423/705 |
| 6,106,803 A | | 8/2000 | Hasenzahl et al. | |
| 2001/0021369 A1 | * | 9/2001 | Lin et al. | 423/713 |

FOREIGN PATENT DOCUMENTS

| | | |
|---|---|---|
| BE | 1 001 038 A | 6/1989 |
| DE | 196 23 611 | 12/1997 |
| DE | 196 23 972 A1 | 12/1997 |
| DE | 190 39 782 | 3/2000 |
| EP | 0 325 053 | 7/1969 |
| EP | 0 791 558 | 8/1997 |
| EP | 838431 A1 * | 4/1998 ........... C01B/37/00 |
| EP | 0 906 784 A2 | 4/1999 |
| EP | 0 906 784 A3 | 3/2000 |
| FR | 2 471 950 A | 6/1981 |
| WO | WO 99/28030 | 6/1999 |
| WO | WO 99/52626 | 10/1999 |

OTHER PUBLICATIONS

"Studies on the Synthesis of Titanium Silicalite, TS–1," Thangaraj A et al., Zeolites, US, Butterworth–Heinemann, vol. 12, No. 8, Nov. 1, 1992, pp. 943–9510, XP000198990, ISSN: 0144–2449, 6 pps.

"Preparation of Colloidal Suspensions of Discrete TS–1 Crystals," Zhang, G. et al., Chemistry of Materials, US, American Chemical Society, Washington, vol. 9, No. 1, 1997, pp. 210–217, XP000683976, ISSN: 0897–4756, 8 pps.

"Catalytic Properties of Crystalline Titanium Silicalites," Thangaraj, A. et al., Journal of Catlysis, US, Academic Press, Inc., vol. 130, 1991, pp. 1–8, XP002143172, 8 pps.

International Search Report, dated Jul. 24, 2001, for PCT Application No. PCT/EP01/02118, 3 pps.

\* cited by examiner

*Primary Examiner*—David Sample
(74) *Attorney, Agent, or Firm*—Smith, Gambrell & Russell, LLP

(57) ABSTRACT

The present invention concerns a method for the production of a titanium-containing zeolite whereby a synthesis gel is formed by combining and hydrolysing a hydrolysable silicon compound, a hydrolysable titanium compound and a basic quaternary ammonium compound in an aqueous medium, in quantities such that relative to the starting compounds the molar ratio of Si/Ti is greater than or equal to 30 and that of N/Si is 0.12 to less than 0.20, and the synthesis gel is then crystallised at a temperature of 150 ° C. to 220 ° C. for a period of less than 3 days, and a titanium-containing zeolite obtainable by this method.

19 Claims, No Drawings

METHOD FOR THE PRODUCTION OF A TITANIUM-CONTAINING ZEOLITE

The present invention concerns a method for the production of a titanium-containing zeolite, a titanium-containing zeolite obtainable by this method, a method for the epoxidation of olefins in the presence of a titanium-containing zeolite produced in this way and also the use of such a zeolite as a catalyst for the epoxidation of olefins.

A method for the production of titanium silicalite and also the use of the titanium silicalite as a catalyst in a series of reactions, among them oxidation reactions. is known from U.S. Pat. No. 4,410,501. It describes two different procedures. On the one hand the formation of a synthesis gel starting from a hydrolysable silicon compound such as tetraethyl orthosilicate, for example, or alternatively the use of a colloidal silicon dioxide as silicon source. The first version is described in example 1 of U.S. Pat. No. 4,410,501. Here tetraethyl orthosilicate and tetra-n-propyl ammonium hydroxide (TPAOH) are used in a molar ratio of 0.45, which also corresponds to the preferred range for the molar ratio of ammonium compound to silicon compound as stated in the general part of the description. Common to both versions of the procedure according to the description in U.S. Pat. No. 4,410,501 is a long reaction period for the hydrothermal stage of at least six days.

EP-A 0 838 431 describes a method for the production of titanium-containing zeolites starting from tetraalkyl orthosilicate and tetraalkyl orthotitanate. the key feature of which is that the reaction mixture is reacted in an autoclave under hydrothermal conditions without distilling off the alcohols formed during hydrolysis.

Many groups of researchers in industry and universities have sought to optimise the synthesis of titanium silicalite, in terms of both the activity of the resulting catalyst and the efficiency of the method, i.e. reducing the length of the hydrothermal stage, improving yields, etc., starting from the teaching of U.S. Pat. No. 4,410,501.

Thus in "Applied Catalysis A: General, 92(1992) 93–111" A. J. H. P. van der Pol and J. H. C. van Hooff examined the influence of $SiO_2$ source, crystallisation time, crystallisation conditions and ratio of ammonium compound/silicon and silicon/titanium on titanium silicalite synthesis and on the activity of the resulting catalyst. In these experiments both the method, starting from tetraethyl orthosilicate, and the variant, starting from a colloidal silicon dioxide, were investigated. A comparison of these two methods already shows that a higher ratio of ammonium compound to Si has to be used for the ester method, i.e. use of tetraethyl orthosilicate. This corresponds in this respect to the teaching of U.S. Pat. No. 4,410,501, where a markedly higher ratio of ammonium to silicon is likewise used for the orthosilicate route. It further emerges that, irrespective of the method used, crystallisation times of two days are sufficient for the production of the catalyst. This publication further teaches that a titanium silicalite produced using orthosilicate displays a markedly higher catalytic activity than catalysts produced using colloidal silicon dioxide. A substantial part of the above publication deals with the question of how the reaction conditions, particularly the ratios of the starting compounds, should be selected in order to produce the smallest possible primary crystallites in the catalyst. The influence on crystallite size of the ratio of ammonium compound to silicon in the starting compounds was examined in particular. It was determined that the molar ratio of ammonium compound to silicon should be at least 0.22 and should preferably be in the range between 0.3 and 0.35 in order to obtain the desired primary crystallite size. By contrast, the ratio of Si to Ti has virtually no influence on the crystallite size of the titanium silicalite.

These results were confirmed by a further investigation by van der Pol, Verduyn and van Hooff in "Applied Catalysis A: General, 92 (1992) 113–130". Here the activity of various titanium silicalite catalysts was examined during the hydroxylation of phenol. It was determined that activity is a function of crystallite size and increases as the crystallite size reduces. The crystallite size in turn depends on the ratio of ammonium to silicon, whereby a ratio of 0.35 will lead to a crystallite size of 0.2 μm and shows the greatest activity. Higher ratios of ammonium to silicon of 0.53 or 0.78 lead to significantly larger crystallites and lower activities. A lower ratio of 0.22 likewise leads to larger crystallites and likewise to a drop in activity.

These studies further show that in the investigated range of ratios of ammonium compound to silicon, the proportion of incorporated titanium remains practically constant with a constant ratio of silicon to titanium compound in the starting composition.

These studies led to the development of a standard synthesis for a titanium silicalite catalyst that was given the name of EUROTS-1 catalyst and whose synthesis is disclosed in J. A. Martens et al. in "Applied Catalysis A: General, 99 (1993) 71–84". In the synthesis of EUROTS-1, tetraethyl orthosilicate, tetraethyl orthotitanate and tetrapropyl ammonium hydroxide are combined in a molar ratio of Si to Ti of 35, ammonium to Si of 0.36 and $H_2O$ to $SiO_2$ of 28.2, hydrolysed and crystallised for four days at 175° C.

Nevertheless, despite this very extensive and detailed examination of the parameters that influence the synthesis and activity of titanium silicalite catalysts and the development of a highly active standard catalyst as described above, there is still a need within the industry to synthesise titanium silicalite catalysts efficiently and more cost effectively and, if possible, also to increase the activity of the catalyst, particularly for the epoxidation of olefins.

The object of the present invention is therefore to provide a more efficient and more cost-effective method for the production of titanium-containing zeolites, without impairing the catalytic activity of the resulting zeolite. A further object is to provide a titanium-containing zeolite with an improved activity for the epoxidation of olefins with hydrogen peroxide.

This object is achieved by a method for the production of a titanium-containing zeolite, whereby a synthesis gel is formed by combining and hydrolysing a hydrolysable silicon compound, a hydrolysable titanium compound and a basic quaternary ammonium compound in an aqueous medium, in quantities such that relative to the starting compounds the molar ratio of Si/Ti is greater than or equal to 30 and that of N/Si is 0.12 to less than 0.20, and the synthesis gel is then crystallised at a temperature of 150° C. to 220° C. for a period of less than 3 days, and by a titanium-containing zeolite obtainable by such a method.

According to the present invention a hydrolysable silicon compound and a hydrolysable titanium compound are first hydrolysed with a basic quaternary ammonium compound in the presence of water. The key feature here is that the starting compounds are reacted in specific molar ratios to one another. The molar ratio of Si to Ti in the starting compounds can be varied within broad limits, provided that it is ≧30. By contrast, the molar ratio of N to Si in the starting compound must be kept within the narrow range of 0.12 to <0.20.

It was surprisingly established that although in this range of the molar ratio of N to Si the crystallite size increases markedly in comparison to the ratio of 0.35 that was regarded as being optimum according to the teaching of A. van der Pol and J. H. C. van Hooff (loc. cit.), the catalyst activity in a propylene epoxidation reaction with hydrogen peroxide nevertheless increases in this narrow range in contrast to the teaching established by van der Pol and van Hooff. Without feeling committed to a particular theory, it is assumed that this effect is achieved by proportionately more titanium being incorporated into the crystal structure of the zeolite in the cited range for the molar ratio of N to Si with a constant ratio of Si to Ti. The associated increase in activity overcompensates for the loss in activity due to the increase in the primary crystallite size. This result is all the more surprising since van der Pol and van Hooff (loc. cit.) have shown that with an N to Si ratio of 0.22 and above, if the Si to Ti ratio in the starting compounds remains constant, the quantity of titanium incorporated into the zeolite remains constant and is substantially independent of the N to Si ratio.

Particularly good results in terms of catalyst activity in epoxidation reactions are achieved with a molar ratio of N to Si in the starting compounds in the range from 0.12 to 0.17 especially in a range of 0.12 to less than 0.17, preferably from 0.12 to 0.16.

Particularly suitable as hydrolysable silicon or titanium compounds for the method according to the invention are the tetraalkyl orthosilicates or tetraalkyl orthotitanates, whereby alkyl is preferably selected from the group consisting of methyl, ethyl, propyl or butyl. The most preferred starting compounds are tetraethyl orthosilicate and tetraethyl orthotitanate.

The quaternary ammonium compound is a template compound that determines the crystal structure by absorption in the crystal lattice of the product during crystallisation. Tetraalkyl ammonium compounds such as tetraalkyl ammonium hydroxide, particularly tetra-n-propyl ammonium hydroxide, are preferably used-to produce titanium silicalite-1 (MFI structure), tetra-n-butyl ammonium hydroxide to produce titanium silicalite-2 (MEL structure) and tetraethyl ammonium hydroxide to produce titanium-β-zeolite (BEA crystal structure). The quaternary ammonium compound is preferably used as an aqueous solution.

The pH value for the synthesis sol of >9, preferably >11, that is necessary for synthesis is adjusted by the basic-reacting quaternary ammonium compound.

The temperature at which the synthesis sol is produced can be selected between broad limits, but the mixture of hydrolysable silicon compound and hydrolysable titanium compound is preferably cooled to a temperature in the range from 0° C. to 10° C., preferably 0° C. to 5° C., and the basic quaternary ammonium compound in an aqueous solution cooled to the same temperature is then added dropwise. According to an alternative embodiment, tetraethyl orthosilicate and tetraethyl orthotitanate are heated to 35° C. before hydrolysis and stirred at this temperature for 30 minutes in order to achieve complexation between the two products (precondensation). This precondensation has no noticeable influence on the catalytic properties of the end product, however.

In a further embodiment of the present invention, where tetraalkyl orthosilicates and tetraalkyl orthotitanates are used as silicon or titanium source respectively, the alcohol produced during hydrolysis is distilled off as a water azeotrope. In some cases it can then be advisable to replace the volume of alcohol/water azeotrope removed from the reaction mixture by distillation at least in part by water in order to avoid the formation of a solid gel or of wall deposits during crystallisation.

The synthesis sol, optionally after an additional maturing period, is then crystallised under autogenous pressure, at a temperature of 150° C. to 220° C., preferably 170° C. to 190° C. (hydrothermal synthesis). Under the specified conditions of the method according to the invention the crystallisation time is less than 3 days, preferably less than 24 hours, particularly preferably a maximum of 12 hours.

According to a preferred embodiment of the method according to the invention, the quantities of the starting compounds are selected such that relative to the starting compounds a molar ratio for $H_2O$ to Si is established in the range from 10 to 20, preferably 12 to 17. It is particularly advantageous if the molar ratio of $H_2O$ to Si in the synthesis gel before hydrothermal synthesis, i.e. after the possible at least partial replacement by water of the water-alcohol azeotrope optionally distilled off after hydrolysis, is adjusted in the range from 15 to 42, preferably 15 to 35. It was surprisingly established that despite this very small quantity of water the procedure and the catalytic activity of the resulting product are not impaired. By contrast, it was found that a molar ratio of water to Si in the above range combined with the molar ratio according to the invention of ammonium compound to Si in the starting composition leads to an active catalyst. One reason for this could be the high concentration of quaternary ammonium compound in the synthesis gel despite markedly reduced quantities of ammonium compound in the starting compound due to the similarly small quantities of water.

A further advantage of the small quantity of water lies in the markedly increased yield of titanium-containing zeolite per kg of synthesis gel as compared with the prior art, making the overall method more efficient and cost-effective.

The crystals produced after the hydrothermal stage have a primary crystal size in the range from 0.2 to 2.0 μm, preferably from 0.3 to 1.5 μm, and are separated from the parent liquor by filtration, centrifugation or decantation and washed with a suitable washing liquid, preferably water. The crystals are then optionally dried and calcined at a temperature of between 400° C. and 1000° C. preferably between 500° C. and 750° C., to remove the template.

According to a preferred embodiment of the present invention the crystal suspension is neutralised after the hydrothermal stage and before separation of the crystals. The crystal suspension as formed after completion of crystallisation in the method according to the invention is alkaline because of the excess of basic quaternary ammonium salt and generally displays a pH greater than 12. If the pH value of the suspension is reduced to a value from 7 to 10, preferably from 7 to 8.5, a greater agglomeration of primary crystallites is observed. This greatly improves the filterability of the suspension, such that separation can be performed with standard membrane filters without breaking through of the product and with conventional filtration times. This preferred embodiment can thus further increase the efficiency of the method according to the invention.

The pH value of the crystal suspension can be reduced either by the addition of acid, such as e.g. mineral acids or organic acids, after 25 completion of the hydrothermal stage or by crystallisation at elevated temperatures, e.g. at 200° C. to 220° C. In the latter case the quaternary ammonium compound, e.g. tetra-n-propyl ammonium hydroxide, is thermally decomposed with consumption of hydroxide ions. Preferred acids are hydrochloric acid and acetic acid.

The lower pH value of the crystal suspension causes the silicates and titanates dissolved within it to be at least partially precipitated, such that the separated titanium-containing zeolite contains a small quantity of titanium compounds that are not incorporated into the lattice. No negative influence on the activity of the resulting catalyst has-been observed, however.

The crystalline titanium-containing zeolites according to the invention are obtained in powder form. For their use as oxidation catalysts they can optionally be converted into a suitable shape for use, such as, for example, micro-pellets, balls, tablets, solid cylinders, hollow cylinders or honeycomb shapes, by known methods for shaping powdered catalysts such as, for example, pelletisation, spray drying, spray pelletisation or extrusion.

The titanium-containing zeolite produced according to the invention can be used as a catalyst in oxidation reactions with $H_2O_2$. In particular the titanium-containing zeolite according to the invention can be used as a catalyst in the epoxidation of olefins by means of aqueous hydrogen peroxide in a solvent miscible with water.

The method according to the invention has the advantage that because of the low ratio of ammonium to silicon relative to the amount of zeolite produced, in comparison to the prior art, a significantly smaller quantity of quaternary ammonium compound, the most expensive of the starting materials used. is required. This has markedly improved the cost-efficiency of the manufacturing process. Furthermore, the yield of product relative to the mass of synthesis gel can be increased if the molar ratio of $H_2O$ to Si relative to the starting compounds can be kept within the stated range. Surprisingly it has been established that, in contrast to the teaching of the prior art, the catalyst activity is not impaired by these measures to optimise the economy of the method but on the contrary a new product is obtained that is characterised by an improved activity in spite of a larger primary crystallite size in comparison to the prior art.

The primary crystallite size of the titanium-containing zeolite produced by the method according to the invention lies in the range between 0.2 and 2.0 $\mu$m, preferably between 0.3 and 1.5 $\mu$m, whereas according to the prior art a crystallite size in the range between 0.1 and 0.2 $\mu$m is described as being the optimum size for catalyst activity. The present invention is illustrated in greater detail by means of the examples:

COMPARATIVE EXAMPLE 1

Production of EUROTS-1

EUROTS-1 was produced by reference to the instructions in Martens et al., "Applied Catalysis A: General, 99 (1993) 71–84". Tetraethyl orthosilicate was placed in a 10 l autoclave rendered inert with nitrogen, tetraethyl orthotitanate was added with stirring and on completion of the addition the resulting mixture was cooled to approx. 1.0° C. A 40 wt. % solution of tetra-n-propyl ammonium hydroxide and deionised water was then added with stirring at this temperature over around five hours by means of a hose pump. The quantities were selected such that the molar ratio of $SiO_2$ to $TiO_2$ is 35, the molar ratio of N to Si is 0.36 and the molar ratio of $H_2O$ to $SiO_2$ is 28.2. Although the reaction solution initially became milky-opaque, the solids formed dissolved again completely as further tetra-n-propyl ammonium hydroxide was added.

In order to complete the hydrolysis and to distil off the ethanol formed, the reaction mixture was heated first to approx. 80° C. and then to max. 95° C. over around 3 hours. The ethanol-water azeotrope distilled off in this way was replaced by the same volume of double-deionised water. The synthesis sol was then heated to 175° C. and kept at this temperature for 12 hours. After cooling of the resulting titanium silicalite suspension, the solid formed was separated by centrifugation from the strongly basic parent liquor still containing tetra-n-propyl ammonium hydroxide, washed and dried overnight at 120° C. and then finally calcined in air at 550° C. for five hours in a muffle furnace.

This results in a consumption of 2.9 kg 40 wt. % tetra-n-propyl ammonium hydroxide solution per kg TS-1 and a yield of 50 g TS-1 per kg synthesis gel with an activity coefficient of 22 $min^{-1}$.

The activity coefficient was determined as follows:

1.0 g of the titanium silicalite catalyst produced in comparative example 1 in 300 ml methanol was then placed in a thermostatically controlled laboratory autoclave with aeration stirrer at 40° C. under a propylene atmosphere and the solvent saturated with propylene at 3 bar overpressure. 13.1 g of 30 wt. % aqueous hydrogen peroxide solution are then added in one portion and the reaction mixture kept at 40° C. and 3 bar, with propylene being made up via a pressure regulator to compensate for consumption by the reaction. Samples were taken at regular intervals via a filter and the hydrogen peroxide content of the reaction mixture determined by redox titration with cerium(IV) sulfate solution. Plotting $\ln(c/c_0)$ against time t, where c is the $H_2O_2$ concentration measured at time t and $c_0$ is the $H_2O_2$ concentration calculated at the start of the reaction, produces a straight line. The activity coefficient was determined from the gradient of the straight line using the equation $$\frac{dc}{dt} = k \cdot c \cdot c_{cat}$$

where $c_{cat}$ stands for the catalyst concentration in kg catalyst per kg reaction mixture.

Example 1

Production of a titanium silicalite 1 according to the present invention.

The procedure described for comparative example 1 was repeated with the exception that quantities of starting compounds were used such that relative to the starting compounds the molar ratio of N to Si was 0.17 and that of $H_2O$ to Si was 13.3. The molar ratio of Si to Ti of 35 was maintained.

This synthesis method resulted in a consumption of tetra-n-propyl ammonium hydroxide (40% solution) of 1.6 kg per kg TS-1, a yield of 110 g TS-1 per kg synthesis gel and an activity coefficient of the resulting catalyst of 31.6 $min^{-1}$ after crystallisation for 12 hours.

This comparison already shows that with a method that uses 50% less of the costly tetra-n-propyl ammonium hydroxide, the yield of catalyst per kg of synthesis gel can be more than doubled and yet, contrary to the expectations of the prior art, a considerable increase in the catalytic activity of the resulting catalyst can be achieved.

Examples 2 and 3

Example 1 was repeated with the ratios of feedstocks as set out in Table 1. The resulting product properties are likewise set out in Table 1.

COMPARATIVE EXAMPLES 2 TO 4

Comparative experiment 1 was repeated with the ratios of feedstocks as stated in Table 1. The product properties of the resulting titanium silicalite-1 samples are likewise summarised in Table 1.

The molar ratio of Si to Ti relative to the starting compounds was kept constant at 35 in all of the experiments.

TABLE 1

| | Ratio of feedstocks | | Product properties of titanium silicalite-1 | | Catalytic |
|---|---|---|---|---|---|
| Example | H₂O/Si (mol/mol) | N/Si (mol/mol) | wt. % TiO₂ | Crystallite size (μm) | activity (min⁻¹) |
| C1 | 28.2 | 0.36 | 2.4 | 0.1–0.2 | 22.1 |
| C2 | 16.8 | 0.10 | 3.0 | 1.0–4.0 | 22.1 |
| C3 | 16.8 | 0.08 | 2.8 | 2–3 | 25.2 |
| C4 | 9.3 | 0.22 | 2.8 | 0.2 | 22.2 |
| 1 | 13.3 | 0.17 | 3.2 | 0.4 | 31.6 |
| 2 | 16.9 | 0.12 | 3.2 | 0.5–1.5 | 34.4 |
| 3 | 16.8 | 0.15 | 3.3 | 0.5 | 32.1 |

The comparison between the examples according to the present invention and the comparative examples shows that the correlation between the ratio of nitrogen to silicon in the starting compounds and the primary crystallite size reflects the progression described in the prior art. The experiments show that an optimum primary crystallite size of between 0.1 and 0.2 μm is achieved with a ratio of N to Si of 28 or higher.

However, in contrast to the predictions from the prior art, a lower molar ratio of N to Si does not lead to a reduction in catalytic activity; on the contrary, the increased incorporation of titanium in the crystal lattice in the examples according to the present invention overcompensates for the negative influence of the increasing primary crystallite sizes on catalyst activity.

The comparison with the synthesis of the EUROTS-1 catalyst (comparative example 1) shows that a catalyst with increased activity can be produced by the method according to the invention, whereby in comparison to the prior art the method leads to a markedly reduced consumption of expensive starting materials such as tetra-n-propyl ammonium hydroxide and to a markedly increased yield of titanium silicate per kg of synthesis gel and hence the cost-efficiency of the synthesis method has also been able to be improved.

Example 4

Example 1 was repeated, whereby the titanium silicate crystals were separated not by centrifugation but by filtration, however. The basic (pH=12.5) crystal suspension was passed through a nutsch filter with a blue belt filter. No solid remained on the nutsch.

Examples 5 and 6

Example 4 was repeated, whereby the pH value of the crystal suspension was reduced to the value stated in Table 2 by addition of hydrochloric acid before filtration. In both cases the titanium silicalite was able to be separated off by means of a nutsch filter with a blue belt filter without breaking through of the product.

As in comparative example 1, the titanium silicate was washed, dried overnight at 120° C. and calcined in air at 550° C. for five hours in a muffle furnace. The product was then analysed for titanium content, qualitatively for non-lattice titanium compounds and for activity as described above. The results are likewise set out in Table 2.

TABLE 2

| | | Product properties | | |
|---|---|---|---|---|
| Example | pH of suspension | Titanium content (wt. % TiO₂) | Content of non-lattice Ti | Activity coefficient (min⁻¹) |
| 5 | 8.5 | 3.2 | + | 29.2 |
| 6 | 7 | 3.5 | +++ | 30.9 |

The content of non-lattice titanium compounds was estimated qualitatively from the intensity of the DR-UV-Vis bands between 250 and 300 nm. The product from example 6 had a higher content of non-lattice titanium compounds than the product from example 5. As the comparison of the activity coefficients of example 5 and 6 with example 1 shows, the reduction in the pH value of the crystal suspension has a negligible influence on the activity of the catalyst.

What is claimed is:

1. A method for the production of a titanium-containing zeolite, comprising forming a synthesis gel by combining and hydrolyzing a hydroyzable silicon compound, a hydrolysable titanium compound and a basic quaternary ammonium compound, as starting compounds in an aqueous medium as a reactive mixture, in quantities such that relative to the starting compounds the molar ratio of Si/Ti is greater than or equal to 30, the molar ratio of H₂O/Si is 10 to 20 and the molar ratio of N/Si is 0.12 to less than 0.20, and crystallizing the synthesis gel in a crystallization stage at a temperature of 150° C. to 220° C. for a period of less than 3 days.

2. The method according to claim 1, wherein the molar ratio of N/Si is 0.12 to less than 0.17.

3. The method according to claim 2, wherein the hydrolyzable silicon compound is a tetraalkyl orthosilicate, and the hydrolysable titanium compound is a tetraalkyl orthotitanate.

4. The method according to claim 1, wherein the molar ratio of H₂O/Si is 12 to 17.

5. The method according to claim 4, wherein the hydrolyzable silicon compound is a tetraalkyl orthosilicate, and the hydrolysable titanium compound is a tetraalkyl orthotitanate.

6. The method according to claim 1, wherein the hydrolyzable silicon compound is a tetraalkyl orthosilicate, and the hydrolysable titanium compound is a tetraalkyl orthotitanate.

7. The method according to claim 6, wherein the hydrolysis of the hydrolysable titanium and silicon compounds is supported by distilling off resulting alcohols and optionally replacing a volume of alcohol removed by distillation at least in part by the addition of water to the reaction mixture.

8. The method according to claim 7, wherein the quaternary ammonium compound is a tetraalkyl ammonium hydroxide.

9. Titanium-containing zeolite produced by the method according to claim 6 having a primary crystallite size of 0.2 to 2.0 μm.

10. A method for the epoxidation of olefins comprising reacting an olefin with aqueous hydrogen peroxide in a solvent miscible with water in the presence of a catalyst which is the titanium-containing zeolite according to claim 9.

11. The method according to claim 1, wherein the quaternary ammonium compound is a tetraalkyl ammonium hydroxide.

12. The method according to claim 1, wherein the quaternary ammonium compound is a tetra-n-propyl ammonium hydroxide.

13. The method according to claim 1, wherein a crystal suspension is formed in the crystallization stage.

14. The method according to claim 13, further comprising adjusting pH value of the crystal suspension from the crystallization stage to a value of 7 to 10.

15. The method according to claim 1, further comprising separating off the titanium-containing zeolite, drying and calcining said titanium-containing zeolite.

16. Titanium-containing zeolite produced by the method according to claim 15 having a primary crystallite size of 0.2 to 2.0 μm.

17. A method for the epoxidation of olefins comprising reacting an olefin with aqueous hydrogen peroxide in a solvent miscible with water in the presence of a catalyst which is the titanium-containing zeolite according to claim 16.

18. Titanium-containing zeolite produced by the method according to claim 1 having a primary crystallite size of 0.2 to 2.0 μm.

19. A method for the epoxidation of olefins comprising reacting an olefin with aqueous hydrogen peroxide in a solvent miscible with water in the presence of a catalyst which is the titanium-containing zeolite according to claim 18.

* * * * *

UNITED STATES PATENT AND TRADEMARK OFFICE
CERTIFICATE OF CORRECTION

PATENT NO.    : 6,841,144 B2
DATED         : January 11, 2005
INVENTOR(S)   : Hasenzahl, Steffen et al.

It is certified that error appears in the above-identified patent and that said Letters Patent is hereby corrected as shown below:

<u>Title page,</u>
Item [75], Inventors, should read as follows:
-- [75]   Inventors:    Steffen Hasenzahl, Hanau (DE); Klaus Heyne, Bruchkobel (DE); Dieter Kneitel, Rodenbach (DE) --

<u>Column 8, lines 33-67, Column 9, lines 1-13, and Column 10, lines 1-10,</u>
Claims 3-19, should be deleted and replaced, to read as follows:
   3.   The method according to claim 1, wherein the molar ratio of $H_2O/Si$ is 12 to 17.
   4.   The method according to claim 1, wherein the hydrolyzable silicon compound is a tetraalkyl orthosilicate, and the hydrolysable titanium compound is a tetraalkyl orthotitanate.
   5.   The method according to claim 2, wherein the hydrolyzable silicon compound is a tetraalkyl orthosilicate, and the hydrolysable titanium compound is a tetraalkyl orthotitanate.
   6.   The method according to claim 3, wherein the hydrolyzable silicon compound is a tetraalkyl orthosilicate, and the hydrolysable titanium compound is a tetraalkyl orthotitanate.
   7.   The method according to claim 4, wherein the hydrolysis of the hydrolysable titanium and silicon compounds is supported by distilling off resulting alcohols and optionally replacing a volume of alcohol removed by distillation at least in part by the addition of water to the reaction mixture.
   8.   The method according to claim 1, wherein the quaternary ammonium compound is a tetraalkyl ammonium hydroxide.
   9.   The method according to claim 1, wherein the quaternary ammonium compound is a tetra-n-propyl ammonium hydroxide.
   10.  The method according to claim 7, wherein the quaternary ammonium compound is a tetraalkyl ammonium hydroxide.
   11.  The method according to claim 1, wherein a crystal suspension is formed in the crystallization stage.
   12.  The method according to claim 11, further comprising adjusting pH value of the crystal suspension from the crystallization stage to a value of 7 to 10.

UNITED STATES PATENT AND TRADEMARK OFFICE
CERTIFICATE OF CORRECTION

PATENT NO. : 6,841,144 B2
DATED : January 11, 2005
INVENTOR(S) : Hasenzahl, Steffen et al.

It is certified that error appears in the above-identified patent and that said Letters Patent is hereby corrected as shown below:

<u>Column 8, lines 33-67, Column 9, lines 1-13, and Column 10, lines 1-10, (cont)</u>
    12.    The method according to claim 11, further comprising adjusting pH value of the crystal suspension from the crystallization stage to a value of 7 to 10.

Signed and Sealed this

Twenty-fourth Day of May, 2005

JON W. DUDAS
*Director of the United States Patent and Trademark Office*

UNITED STATES PATENT AND TRADEMARK OFFICE
CERTIFICATE OF CORRECTION

PATENT NO. : 6,841,144 B2
DATED : January 11, 2005
INVENTOR(S) : Hasenzahl, Steffen et al.

It is certified that error appears in the above-identified patent and that said Letters Patent is hereby corrected as shown below:

<u>Column 9, line 1 through Column 10, line 11,</u>
Claims 13-19 should be deleted and replaced to read as follows:
-- 13. The method according to claim 1, further comprising separating off the titanium-containing zeolite, drying and calcining said titanium-containing zeolite.
    14. Titanium-containing zeolite produced by the method according to claim 1 having a primary crystallite size of 0.2 to 2.0 $\mu$m.
    15. Titanium-containing zeolite produced by the method according to claim 4 having a primary crystallite size of 0.2 to 2.0 $\mu$m.
    16. Titanium-containing zeolite produced by the method according to claim 13 having a primary crystallite size of 0.2 to 2.0 $\mu$m.
    17. A method for the epoxidation of olefins comprising reacting an olefin with aqueous hydrogen peroxide in a solvent miscible with water in the presence of a catalyst which is the titanium-containing zeolite according to claim 14.
    18. A method for the epoxidation of olefins comprising reacting an olefin with aqueous hydrogen peroxide in a solvent miscible with water in the presence of a catalyst which is the titanium-containing zeolite according to claim 15.
    19. A method for the epoxidation of olefins comprising reacting an olefin with aqueous hydrogen peroxide in a solvent miscible with water in the presence of a catalyst which is the titanium-containing zeolite according to claim 16. --.

Signed and Sealed this

Thirtieth Day of August, 2005

JON W. DUDAS
*Director of the United States Patent and Trademark Office*

UNITED STATES PATENT AND TRADEMARK OFFICE
CERTIFICATE OF CORRECTION

PATENT NO. : 6,841,144 B2
APPLICATION NO. : 10/220577
DATED : January 11, 2005
INVENTOR(S) : Steffen Hasenzahl et al.

It is certified that error appears in the above-identified patent and that said Letters Patent is hereby corrected as shown below:

<u>Title pages,</u>
Item [75], Inventors, should read as follows:
-- [75] Inventors: Steffen Hasenzahl, Hanau (DE); Klaus Heyne, Bruchkobel (DE); Dieter Kneitel, Rodenbach (DE) --

<u>Column 8, lines 33-67, Column 9, lines 1-13, and Column 10, lines 1-10,</u>
Claims 3-19, should be deleted and replaced, to read as follows:
-- 3. The method according to claim 1, wherein the molar ratio of $H_2O/Si$ is 12 to 17.
 4. The method according to claim 1, wherein the hydrolyzable silicon compound is a tetraalkyl orthosilicate, and the hydrolysable titanium compound is a tetraalkyl orthotitanate.
 5. The method according to claim 2, wherein the hydrolyzable silicon compound is a tetraalkyl orthosilicate, and the hydrolysable titanium compound is a tetraalkyl orthotitanate.
 6. The method according to claim 3, wherein the hydrolyzable silicon compound is a tetraalkyl orthosilicate, and the hydrolysable titanium compound is a tetraalkyl orthotitanate.
 7. The method according to claim 4, wherein the hydrolysis of the hydrolysable titanium and silicon compounds is supported by distilling off resulting alcohols and optionally replacing a volume of alcohol removed by distillation at least in part by the addition of water to the reaction mixture.
 8. The method according to claim 1, wherein the quaternary ammonium compound is a tetraalkyl ammonium hydroxide.
 9. The method according to claim 1, wherein the quaternary ammonium compound is a tetra-n-propyl ammonium hydroxide.
 10. The method according to claim 7, wherein the quaternary ammonium compound is a tetraalkyl ammonium hydroxide.
 11. The method according to claim 1, wherein a crystal suspension is formed in the crystallization stage.
 12. The method according to claim 11, further comprising adjusting pH value of the crystal suspension from the crystallization stage to a value of 7 to 10.

UNITED STATES PATENT AND TRADEMARK OFFICE
CERTIFICATE OF CORRECTION

PATENT NO. : 6,841,144 B2  
APPLICATION NO. : 10/220577  
DATED : January 11, 2005  
INVENTOR(S) : Steffen Hasenzahl et al.

It is certified that error appears in the above-identified patent and that said Letters Patent is hereby corrected as shown below:

<u>Column 8, lines 33-67, Column 9, lines 1-13, and Column 10, lines 1-10, (cont'd)</u>

13. The method according to claim 1, further comprising separating off the titanium-containing zeolite, drying and calcining said titanium-containing zeolite.
   14. Titanium-containing zeolite produced by the method according to claim 1 having a primary crystallite size of 0.2 to 2.0$\mu$m.
   15. Titanium-containing zeolite produced by the method according to claim 4 having a primary crystallite size of 0.2 to 2.0$\mu$m.
   16. Titanium-containing zeolite produced by the method according to claim 13 having a primary crystallite size of 0.2 to 2.0$\mu$m.
   17. A method for the epoxidation of olefins comprising reacting an olefin with aqueous hydrogen peroxide in a solvent miscible with water in the presence of a catalyst which is the titanium-containing zeolite according to claim 14.
   18. A method for the epoxidation of olefins comprising reacting an olefin with aqueous hydrogen peroxide in a solvent miscible with water in the presence of a catalyst which is the titanium-containing zeolite according to claim 15.
   19. A method for the epoxidation of olefins comprising reacting an olefin with aqueous hydrogen peroxide in a solvent miscible with water in the presence of a catalyst which is the titanium-containing zeolite according to claim 16. --.

This certificate supersedes Certificate of Corrections issued May 24, 2005 and August 30, 2005.

Signed and Sealed this

Third Day of April, 2007

JON W. DUDAS  
*Director of the United States Patent and Trademark Office*